(12) United States Patent
Hur et al.

(10) Patent No.: US 8,794,450 B2
(45) Date of Patent: Aug. 5, 2014

(54) CHANNEL FILTER HAVING SURFACE TOPOLOGY FOR FILTERING MICRO PARTICLES AND METHOD FOR MANUFACTURING SAME

(75) Inventors: Dae-Sung Hur, Gyeongsangbuk-do (KR); Jun-Ha Park, Gyeonggi-do (KR); Chan-Il Chung, Seoul (KR); Jun-Keun Chang, Seocho-gu (KR)

(73) Assignee: Nanoentek, Inc., Seoul (KR)

( * ) Notice: Subject to any disclaimer, the term of this patent is extended or adjusted under 35 U.S.C. 154(b) by 769 days.

(21) Appl. No.: 12/513,189

(22) PCT Filed: Nov. 2, 2007

(86) PCT No.: PCT/KR2007/005532
§ 371 (c)(1),
(2), (4) Date: May 1, 2009

(87) PCT Pub. No.: WO2008/054180
PCT Pub. Date: May 8, 2008

(65) Prior Publication Data
US 2010/0012575 A1    Jan. 21, 2010

(30) Foreign Application Priority Data

Nov. 2, 2006  (KR) .................. 10-2006-0107514

(51) Int. Cl.
*B01D 35/28* (2006.01)
*B01D 67/00* (2006.01)
*G01N 30/90* (2006.01)
*B01L 3/00* (2006.01)

(52) U.S. Cl.
CPC ............ *B01D 67/0062* (2013.01); *G01N 30/90* (2013.01); *B01D 35/28* (2013.01); *B01L 3/502753* (2013.01)
USPC ............... 210/437; 264/219; 216/52; 216/83; 204/450; 204/600; 210/656

(58) Field of Classification Search
CPC ........ B01D 35/28; B01D 35/00; B29C 33/42; B44C 1/22
See application file for complete search history.

(56) References Cited

U.S. PATENT DOCUMENTS 6,478,974 B1    11/2002  Lebouitz et al.
6,479,072 B1 *  11/2002  Morgan et al. ................ 424/443

(Continued)

FOREIGN PATENT DOCUMENTS

JP     18-043704    2/2006
KR  10-2005-0009612  1/2005

OTHER PUBLICATIONS

Office Action from Korean Intellectual Property Office for Korean Patent Application No. 10-2009-7007294, dated Oct. 12, 2011.

(Continued)

*Primary Examiner* — Dirk Bass
(74) *Attorney, Agent, or Firm* — Sherr & Jiang, PLLC

(57) ABSTRACT

Disclosed is a channel filter for separating microparticles, and more particularly to a channel filter which can easily separate a sample having various sized microparticles by using a surface topology. In the disclosed channel filter, a topology having an upward/downward reference height from a sample inlet to an outlet is continuously or discontinuously formed, and thus it is possible to efficiently separate microparticles from a sample liquid.

8 Claims, 11 Drawing Sheets

(56) References Cited

U.S. PATENT DOCUMENTS 6,596,112 B1     7/2003   Ditter et al.
2004/0195099 A1*   10/2004   Jacobson et al. .............. 204/450
2006/0223165 A1*   10/2006   Chang et al. ............... 435/287.1

OTHER PUBLICATIONS

Notice of Allowance, dated Dec. 28, 2012, in corresponding Korean Patent Application No. 10-2009-7007294.

* cited by examiner

CHANNEL FILTER HAVING SURFACE TOPOLOGY FOR FILTERING MICRO PARTICLES AND METHOD FOR MANUFACTURING SAME

CROSS-REFERENCES TO RELATED APPLICATIONS

This application is a U.S. national phase application, pursuant to 35 U.S.C. §371, of PCT/KR2007/005532, filed Nov. 2, 2007, designating the United States and published on May 8, 2008 as WO 2008/054180 A1, which claims priority to Korean Application No. 10-2006-0107514, filed Nov. 2, 2006. The entire contents of the aforementioned patent applications are incorporated herein by this reference.

TECHNICAL FIELD

The present invention relates to a channel filter structure for separating microparticles, and more particularly to a channel filter having a surface topology in such a manner that microparticles can be sequentially separated from a sample including various sized microparticles, a method for manufacturing the same, and an apparatus for separating microparticles using the same.

BACKGROUND ART

In general, a method for separating microparticles includes chromatography, sieving, field-flow fractionation (fff), etc. The sieving indicates a method for separating particles using differences in particle sizes. In the sieving, when liquid including microparticles is dropped on the surface of the sieve, particles may be separated into fine or undersize particles (which pass through sieve openings on the surface of the sieve), and coarse, oversize, or tail particles (which stay on the sieve without passing through the sieve openings). Herein, when the above method employs only one sieve, only unsized fractions with unknown particle size distribution are obtained. In other words, only when the particle size distribution of the relevant material is known, it is possible to know the minimum particle size of the undersize particles and the maximum particle size of the oversize particles. On the other hand, in the case where multiple sieves with different-sized sieve openings are provided in a size order, as material passes through each sieve, different-sized portions are obtained, and herein, maximum and minimum particle sizes of each portion are determined by each sieve opening size. There are patent publications regarding a method for separating microparticles using a sieving method as described above, which include U.S. Pat. No. 6,596,112, invented by Ditter, U.S. Pat. No. 4,256,693 invented by Kondo and Kitajima, U.S. Pat. No. 4,477,575 invented by Vogel, U.S. Pat. No. 5,139,685 invented by De Castro, etc. However, in such a conventional sieving method, it cannot be said that required particle sizes are clearly separated because there is a probability that rod-shaped particles pass through smaller sieve openings, and the respective sieve openings can have unequal sizes. In addition, in the conventional sieving method, a multi-layered sieve is required, and especially, a sieve for analyzing microparticles is required to be precisely manufactured. Accordingly, there has been a problem in that the manufacture is complicated, and high cost is required.

On the other hand, field-flow fractionation, that is, a method for separating colloids, particle material, and polymers, and estimating the size distribution of the same, was originally theorized by J. Calvin Giddings in 1966. In separating of polymers and minute colloid particles, a quick and selective method was required, and also, in liquid chromatography, it was required to minimize adsorption or shear degradation of a test sample in a stationary phase. Therefore, the field-flow fractionation was developed. The separation by the field-flow fractionation is similar to the chromatography in terms of the principle of using an elution technology, but does not require a stationary phase. In addition, the field-flow fractionation is referred to as one-phase chromatography because a moving phase of the test sample is distributed with different speed ranges within a channel. The range of the test sample, which can be separated by the field-flow fractionation, is about $10^3 \sim 10^{14}$ of molecular weight, and is within about 100 μm of particle size. As such a test sample, various materials widely spread over industries, such as biomaterials including protein, liposome, all kinds of polymer (organic or water-soluble) and latex particles, metal particles, paint particles, and particles related to environmental pollution, can be utilized. There are patent publications regarding the field-flow fractionation, which include U.S. Pat. No. 5,160,625 invented by Jonsson and Carlshaf, and U.S. Pat. No. 4,894,146 invented by Giddings, etc. The channel used for the field-flow fractionation has a shape of a narrow tube with a rectangular cross section, which is formed by inserting a spacer between two flat plates and engaging them with each other. The fractionation is performed by interacting parabolic flow between the two surfaces with external field perpendicular to the flow. In other words, in the field-flow fractionation, the force applied from the outside is driving force for the fractionation. When the external field is applied, a test sample within a channel moves toward an accumulation wall, and at the same time is carried toward the flow from the accumulation wall by Brownian diffusion. Therefore, both movements are mutually balanced, and the test sample is in a steady state in a position very close to the accumulation wall. Herein, small particles are more widely diffused than large particles, and thus are in equilibrium in a higher position from the accumulation wall in the channel. Due to the characteristic of the parabolic flow, the small particles in a relatively high-speed flow move at a high speed. Therefore, small particles are eluted first, and then large particles are eluted later. The above described mode is called a normal mode, which is a typical operation mode of the field-flow fractionation. On the other hand, particles of a size larger than 1 μm are hardly influenced by Brownian diffusion. Herein, large particles have a higher central position than that of small particles, and thus are carried by a high-speed flow. Therefore, the separation order is the reverse of the normal mode. Such an operation phenomenon is called a steric mode. The field-flow fractionation is classified into a variety of subtechniques according to a type of an external field or driving force, such as sedimentation field-flow fractionation (fff) using centrifugal force, flow fff using secondary flow, thermal fff using thermal diffusion with temperature differences, electrical fff using an electric field, etc. Herein, physical characteristics of a test sample, such as molecular weight, strokes radius, density, electrical properties, thermal diffusion coefficient, etc. may be optionally utilized. In addition to such operational variety, in the field-flow fractionation, it is possible to easily, quickly and exactly adjust the stay of a test sample by appropriately adjusting the strength of an external field, and also, it is theoretically possible to estimate the stay by calculating flow speed, and the strength of the field applied to the test sample. Also, field-programming for gradually decreasing the strength of the external field allows effective separation of a test sample with wide size-distribution. Also, in such a method, an eluted sample is not destroyed. Accordingly, the test sample, which has passed through a detector, may be collected as narrow fractions, and then, may be used for a secondary analysis using other analysis mechanisms including a microscope, elementary analysis, etc. However, due to the structure characteristics in the field-flow fractionation, an external field of very high strength may interact with biomaterials. In addition, the fractionation is not economical because the manufacturing of a channel is not easy, and an additional device for generating an external field is required.

In order to solve the above-mentioned problems, a channel having a surface topology was manufactured, and a sample including various sized microparticles was filtered. As a result, it was found that the various-sized microparticles are sequentially separated by the surface topology.

DISCLOSURE

Technical Problem

The present invention provides a channel filter structure for separating microparticles, in which a surface topology having a reference height corresponding to an average of diameters of the microparticles is formed on the surface of a substrate.

Also, the present invention provides a channel filter structure for sequentially separating different microparticles, in which a surface topology is formed on the surface of a substrate, and the height of the surface topology is continuously/discontinuously lowered or raised from a sample inlet to a sample outlet according to the sizes of various microparticles included in a sample.

Also, the present invention provides an apparatus for separating microparticles, the apparatus including a channel filter having a surface topology formed on the surface of a substrate.

Also, the present invention provides a method for manufacturing a channel filter having a surface topology formed on the surface of a substrate.

Technical Solution

In accordance with an aspect of the present invention, there is provided a channel filter structure including a topology that has a reference height corresponding to an average of diameters of microparticles to be separated, on the surface of a substrate. According to another aspect of the present invention, there is provided a channel filter structure including a topology having an inclined height, on the surface of a substrate. Specifically, the reference height of the surface topology is upwardly/downwardly inclined according to the movement direction of a sample, from an inlet through which a sample including different sized microparticles is loaded, to an outlet through which a sample is discharged. Also, the surface topology according to the present invention may be continuously or discontinuously formed in a channel. When the surface topology of the channel filter is changed, the different sized particles included in the sample are sequentially filtered according to particle sizes, during the movement from the sample inlet to the sample outlet.

In the present invention, a topology indicates a phase formed on the surface of a substrate. (See FIG. 1a)

In the present invention, a height of a topology indicates the difference between a wave crest and a wave trough, which is generated by a topology (i.e. phase) formed on the surface of a substrate, and a reference height indicates the average of the height on a predetermined area of the channel substrate surface. (See FIG. 1a)

In the present invention, a width of a topology indicates the distance between a wave crest and its adjacent wave crest, which is generated by a topology (i.e. phase) formed on the surface of a substrate. (See FIG. 1a)

FIGS. 1a and 1b illustrate a concept of a channel filter according to the present invention. As shown in FIG. 1a, a channel filter substrate includes a surface topology having a height (H) corresponding to a particle size of a sample to be separated. In a surface topology, the ratio of a reference height to an average of diameters of separated particles is preferably 1:1~0.5:1 (a topology height: a particle diameter). Also, preferably, as the height of a topology formed on a substrate surface increases, the width (L) generated by a topology (i.e. phase) increases, and also, as the height decreases, the width decreases.

In the present invention, the height (H) of a surface topology may be randomly formed. Accordingly, a wave crest and a wave trough forming the phase of a surface topology may be irregular, and do not have a fixed pattern. In this manner, a wave or a width (L) forming the phase of a topology may also have various values.

Also, in the present invention, the reference height generated by the surface topology may be upwardly/downwardly inclined according to the movement direction of a sample, from a sample inlet to a sample outlet.

Also, in the present invention, the surface topology may be continuously or discontinuously formed according to a channel for filtering.

In an embodiment, by using a microchip having a channel filter according to the present invention, microparticles in a blood sample, such as white blood cells (WBC), red blood cells (RBC), red blood cell clots, platelets, serum, and plasma, were separated. A microchip channel filter was formed in such a manner that a reference height of a surface topology was set to the height of a white blood cell or a red blood cell clot (included in a blood sample) having the largest particle size. In a microchip channel filter formed as described above, a blood sample was loaded as shown in FIG. 1b, and was moved to an outlet by a capillary action. As a result, only white blood cells and red blood cell clots, which have diameters corresponding to the reference height, were trapped by the microchip channel filter, and the remainders, such as red blood cells, platelets, serum, and plasma, etc., were separated. (See FIG. 1c)

A channel filter according to another embodiment of the present invention has a structure where a reference height of a surface topology is sequentially lowered from a sample inlet to a sample outlet. FIG. 2a illustrates the separation of microparticles from a blood sample by using a channel filter of which a reference height is lowered. In FIG. 2a, an inlet (I) has a structure of a relatively high surface-topology reference height, and an outlet has a structure of a relatively low surface-topology reference height. Also, a reference height of the surface topology is sequentially lowered from the sample inlet to the sample outlet. FIG. 2b illustrates the separation of the microparticles from the blood sample by using the channel of FIG. 2a. When the blood sample including various sized particles, such as white blood cells (WBC), red blood cells (RBC), red blood cell clots, platelets, serum, plasma, etc., is loaded to a channel, the microparticles are sequentially filtered by the channel filter or passed through the channel in a size order. In other words, while the sample is moved by a capillary action, from the sample inlet of a high reference height to the sample outlet of a low reference height, white blood cells of a large particle size, red blood cells, and platelets are filtered in a size order at an inlet, a middle portion, and an outlet, respectively, and serum or plasma may be separated and discharged.

FIG. 3 illustrates the result of the loading of a blood sample to a channel filter having a reference height of 10 µm. As shown in FIG. 3, it is found that white blood cells and red blood cells are filtered at a channel filter area.

FIG. 4 illustrates conventional filters and size distribution of sample particles. FIG. 5 illustrates channel filters having a surface topology according to the present invention, and size distribution of sample particles. As noted from FIG. 4, each of the conventional filters has a size smaller than that of the sample particles, and usually has a uniform size. In the conventional filter structure, a filtered portion is too little due to a uniform filter size, and thus the samples may be damaged by pressure drop during filtering. On the other hand, in the case of a filter according to the present invention as shown in FIG. 5, the size of each filter may be variable on the basis of a reference height. Accordingly, in such a filter, there exists a portion having a larger size than that of the sample particles to be separated, and thus, an effective filtering range may be widened, thereby improving the filtering efficiency, and preventing the pressure drop during filtering.

FIGS. 6a and 6b illustrate the distribution of a surface topology according to the present invention, wherein 6a shows an atomic force microscope (AFM) image of a channel filter having a surface topology according to the present invention, and 6b is a measurement result on height/range distribution of the surface topology of the channel of FIG. 6a. As shown in FIGS. 6a and 6b, a topology height of a filter having the surface topology according to the present invention may be variably adjusted on the basis of a certain reference height.

FIGS. 7 to 9 illustrate an experimental result of 10 µm of beads (the size similar to white blood cells) and 3 µm of beads (the size similar to red blood cells).

FIG. 10 schematically illustrates an apparatus for separating microparticles, which has a channel filter of which a reference height of a surface topology is gradually varied. FIG. 10a is a picture of a microchip including a channel filter according to the present invention, and FIG. 10b is an enlarged picture of a channel filter, in which a reference height is sequentially lowered from a sample inlet to a sample outlet. FIGS. 10c and 10d are enlarged pictures of a surface having a reference height of 10 µm.

FIG. 11 schematically illustrates a process for manufacturing a channel filter according to the present invention. When a topology is formed by surface etching, the depth of the surface etching may be variable in order to form an upward or downward inclined reference height of a surface topology. Also, the increase or decrease of a reference height may be continuous or discontinuous, and may be repeated in a channel filter.

The reference height of a surface topology of a channel filter may be adjusted by varying an etching time at a certain etchant concentration. In the present invention, sulfuric acid is used for the etching process. For example, when relatively large-sized microparticles (such as a white blood cell) are separated, the etching process is performed for a relatively long time. On the other hand, when relatively small-sized microparticles are separated, the etching process may be performed for a shortened time. In other words, the reference height of a surface topology may be adjusted by adjusting an etching time. In addition to the chemical etching as described above, a surface topology of a channel filter may be formed by using a physical etching technique in which abrasive of a certain size is applied and polished to a metal surface. The method for forming a surface topology is not limited. For example, when a mold for a surface topology having a certain reference height is manufactured, a channel filter may be manufactured by injection molding.

Advantageous Effects

As described above, by using a channel filter according to the present invention, it is possible to easily separate microparticles from a sample including various sized microparticles. In a channel filter according to the present invention, since a height and a width of a surface topology are randomly formed, sample particles trapped by a filter are trapped over the entire filter, thereby preventing pressure drop and sample damage. Also, due to easy and simple manufacturing process, the channel filter according to the present invention can be manufactured with a low cost.

DESCRIPTION OF DRAWINGS

The foregoing and other objects, features and advantages of the present invention will become more apparent from the following detailed description when taken in conjunction with the accompanying drawings in which.

MODE FOR INVENTION

Hereinafter, exemplary embodiments of the present invention will be described. However, the present invention is not limited to the embodiments, and also, it will be understood that changes, obvious to those skilled in the art, may be made within the scope and spirit of the appended claims.

EXAMPLES

Example 1

Figure 1:
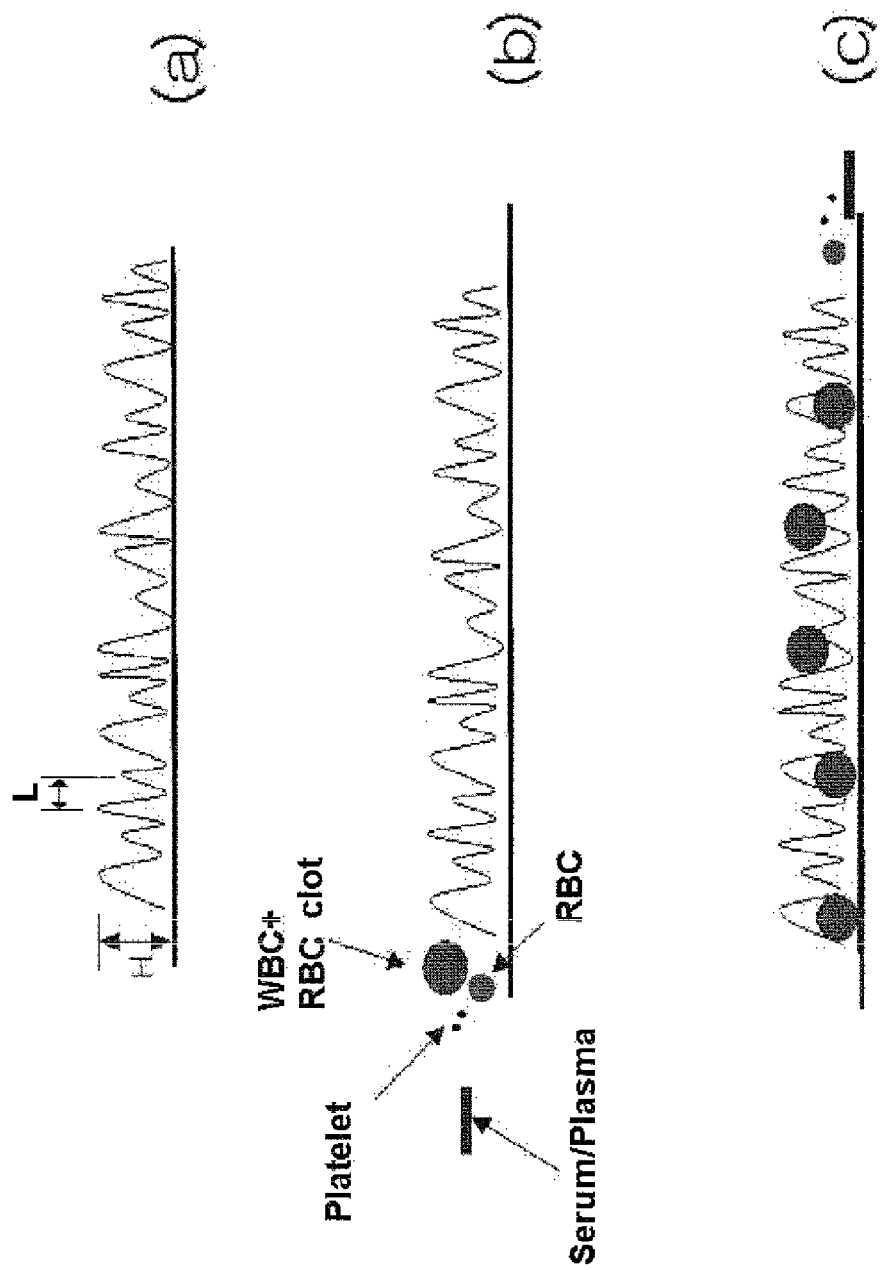
FIGS. 1a to 1c illustrate a channel filter according to an embodiment of the present invention.
Figure 2:
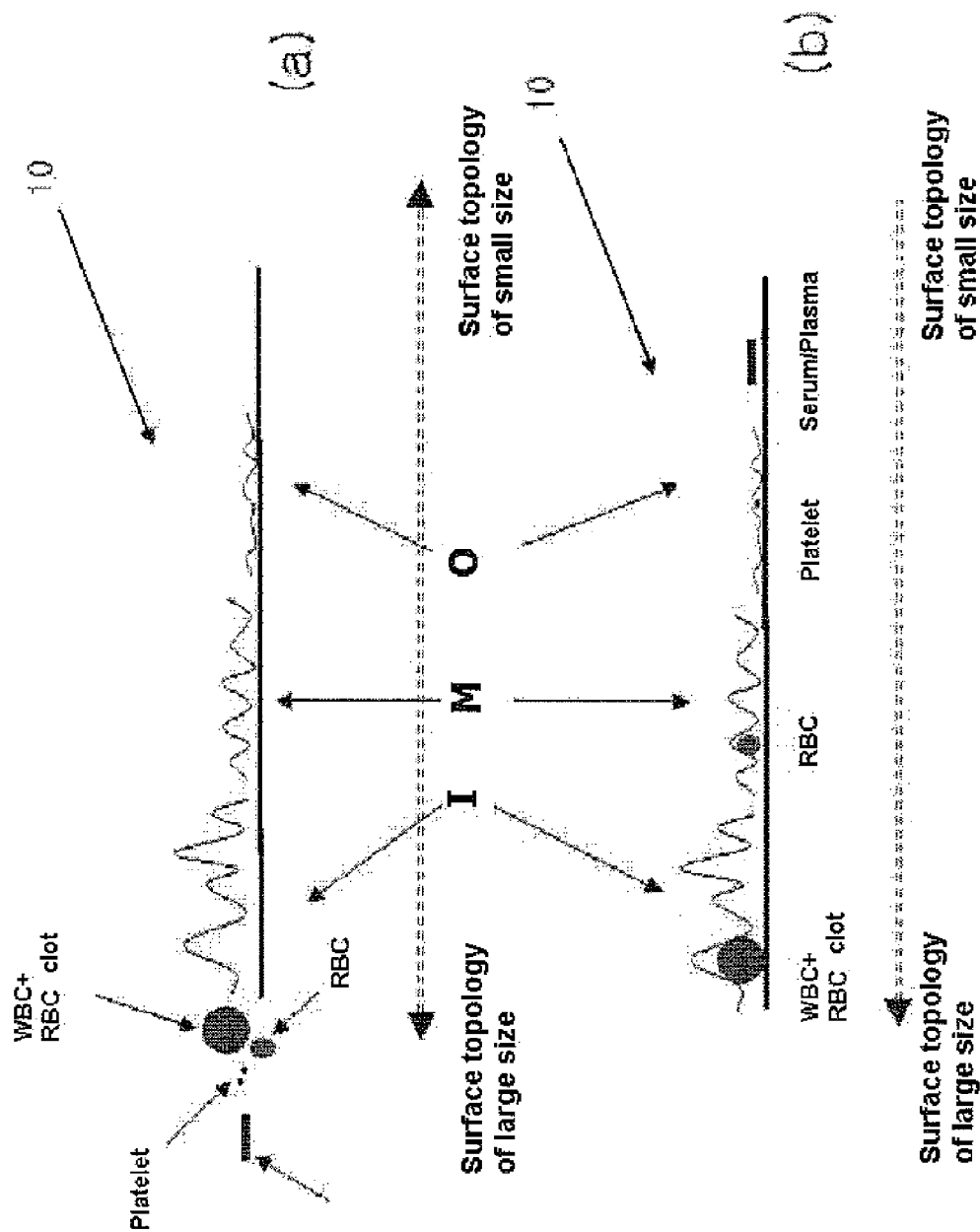
FIGS. 2a and 2b illustrate a channel filter according to another embodiment of the present invention.
Figure 3:
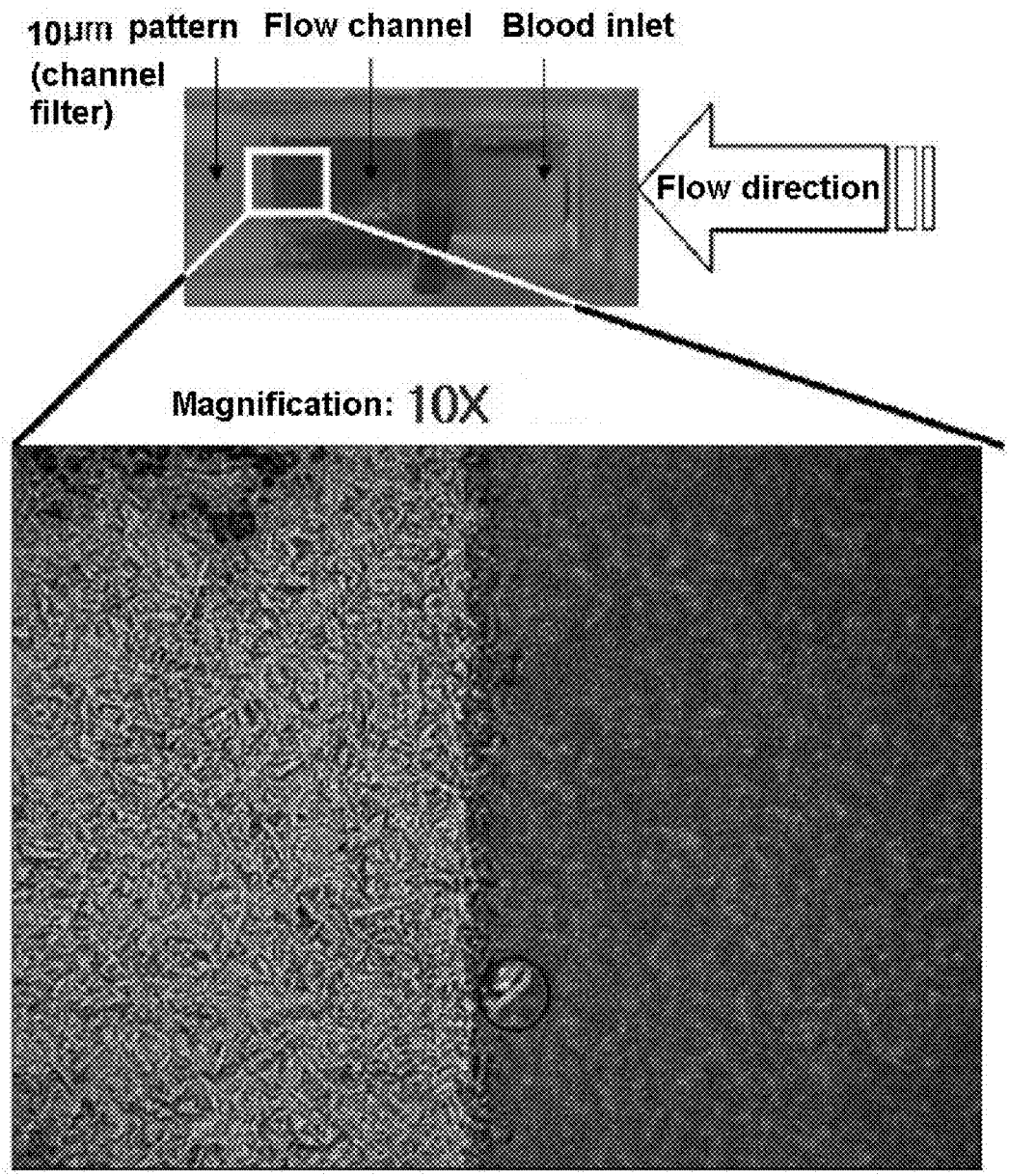
FIG. 3 illustrates the result of separating red blood cells and white blood cells from a blood sample by using a channel filter having a surface topology with a reference height of 10 µm.
Figure 4:
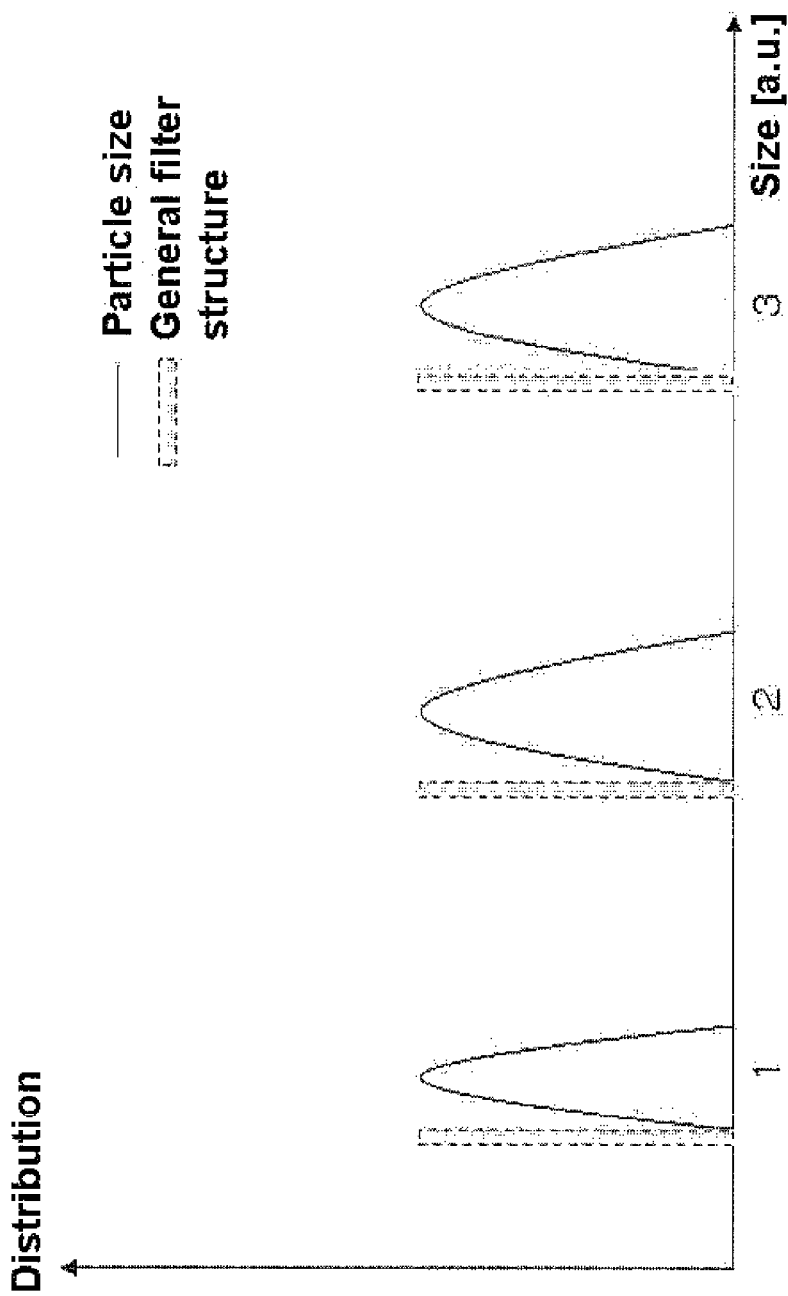
FIG. 4 is a graph for comparing a surface topology structure according to the present invention with a general filter structure.
Figure 5:
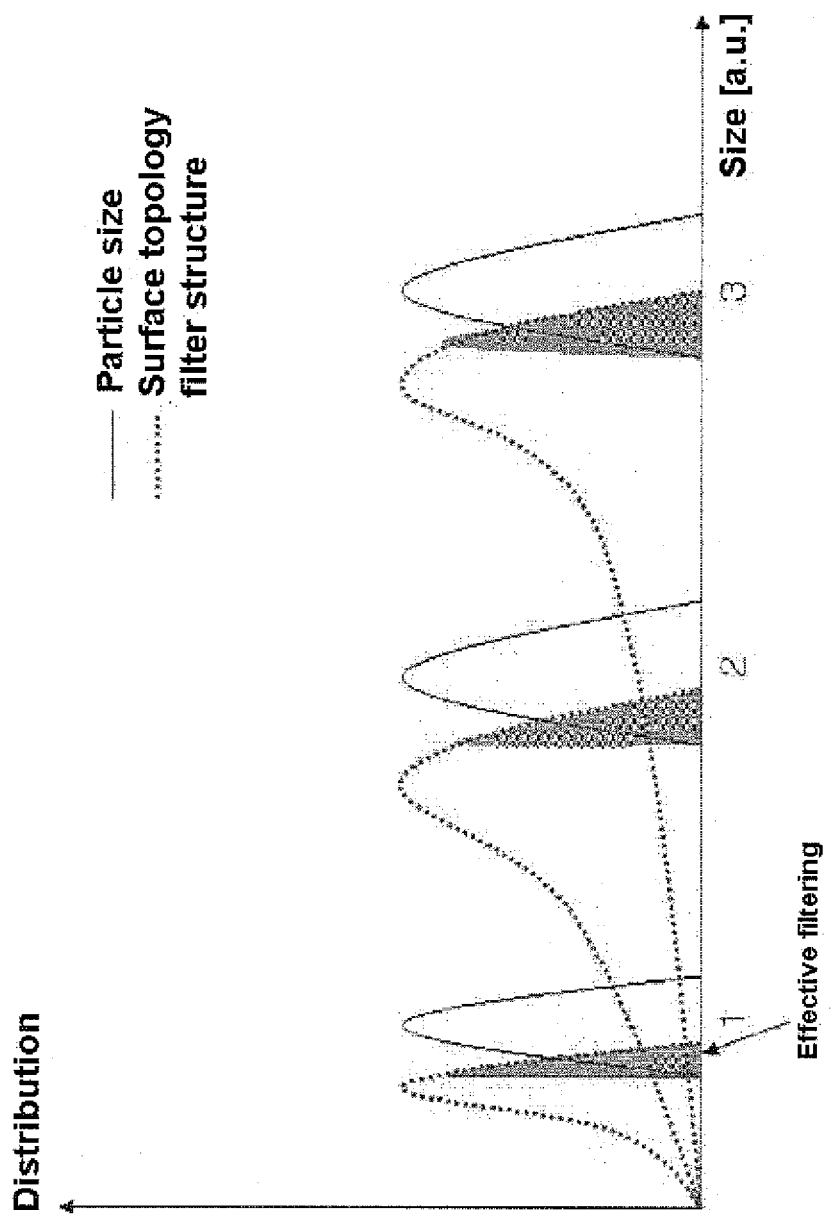
FIG. 5 is a graph for comparing a surface topology structure according to the present invention with a general filter structure.
Figure 6:
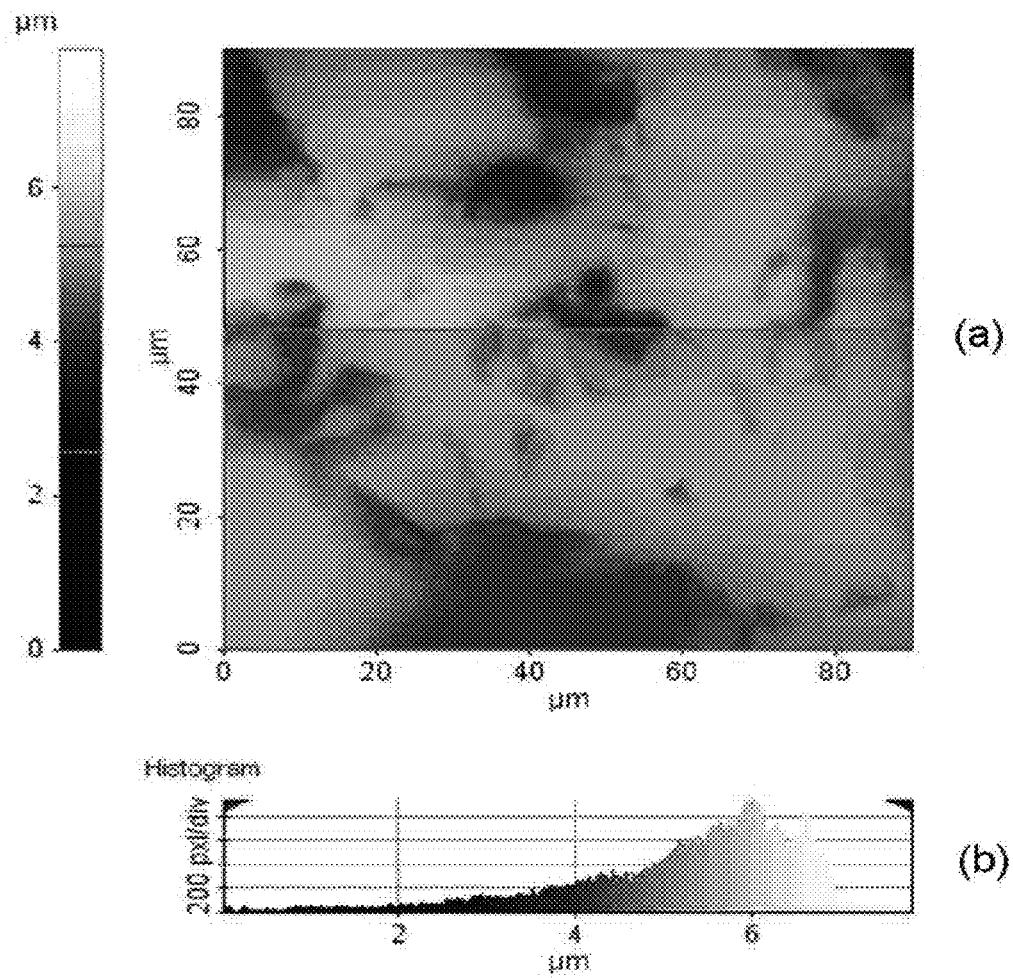
FIGS. 6a and 6b illustrate a reference height and a width distribution of a surface topology according to the present invention, wherein 6a shows an AFM image of a filter structure having a surface topology according to the present invention, and 6b is a measurement result of a reference height and a height distribution of the surface topology.

Separation of Microparticles from a Blood Sample by Using a Channel Filter Having a Topology with a Reference Height of 10 µm A channel filter including a topology with a reference height of 10 µm on a substrate was made by using acrylic (PMMA) substrate and sulfuric acid (as etchant, Sigma-Aldrich). A metallic surface of the substrate, except for a portion for a topology, was covered with a protection film, and was corroded by using a sulfuric acid solution. Then, a pattern was formed on a required surface by plastic (acrylic) injection molding of the metal. The upper plate and the lower plate were bound to each other by solvent, thereby creating a channel filter. Through this process, a microfluidics chip having a channel filter was manufactured. Next, a blood sample of 5 µl was loaded into a channel filter inlet by a pipette, and was moved to a sample outlet by a capillary action. After the movement, the sample was observed by using an optical microscope (Olympus, x10). FIG. 3 shows the observed result. As shown in FIG. 3, red blood cells of about 3 µm and white blood cells of about 10 µm was completely filtered by the channel filter.

From the result shown in FIG. 3, the separation efficiency was calculated by the following formula:

Separation efficiency=(the number of cells in a channel area the number of cells in a filter area)/(the number of cells in a channel area)×100

It was measured that the average number of cells in the channel area was 150, the average number of cells in the channel filter area was 10, and thus the separation efficiency was about 93%. Therefore, considering that a channel having a lower reference height than that of the present example is used, it is expected that the separation efficiency of microparticles from whole blood can be above about 95% when a channel filter according to the present invention is used.

Example 2

Figure 7:
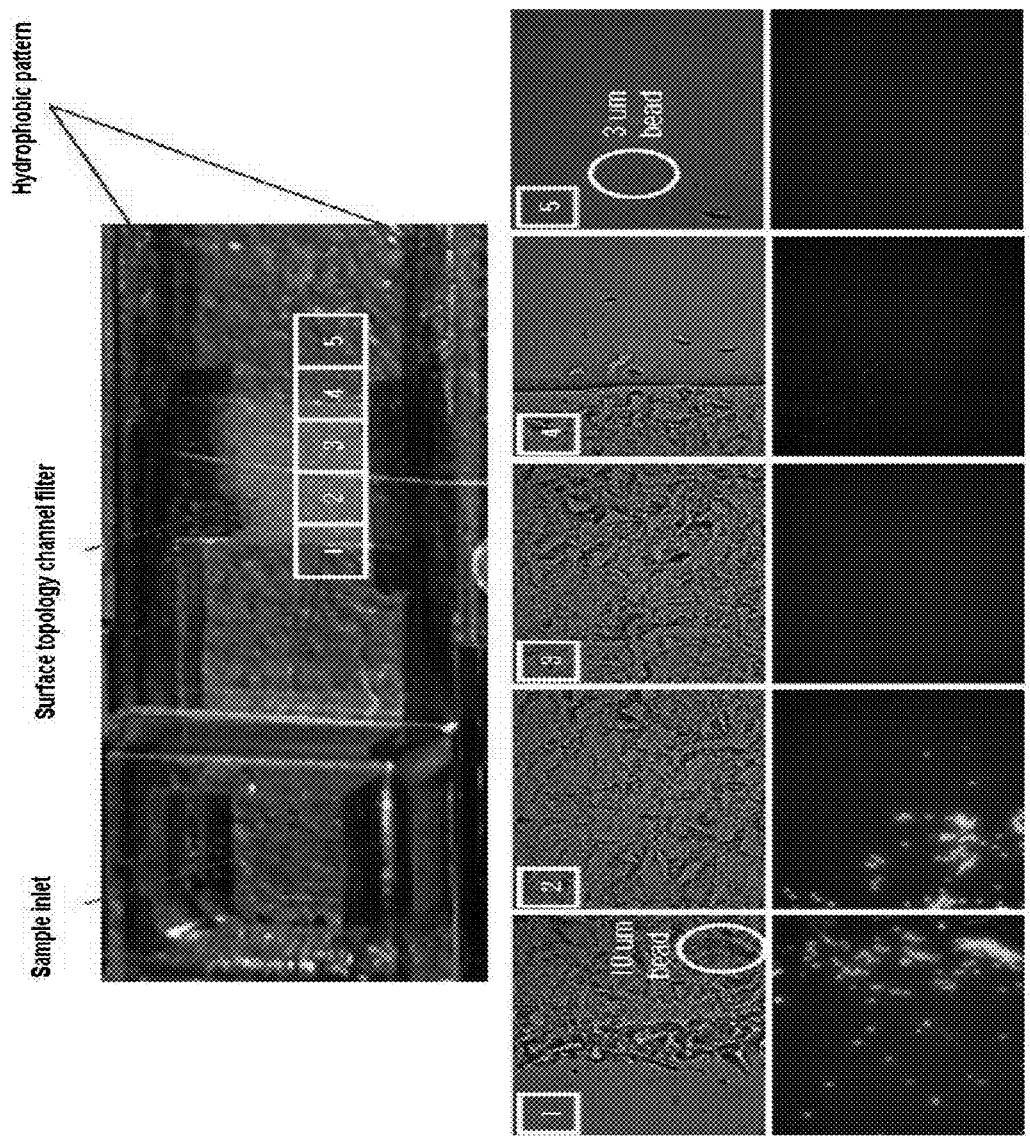
FIGS. 7 to 9 illustrate the result of filtering 10 µm and 3 µm beads from a sample by using a channel filter having a surface topology with a reference height of 10 µm.
Figure 8:
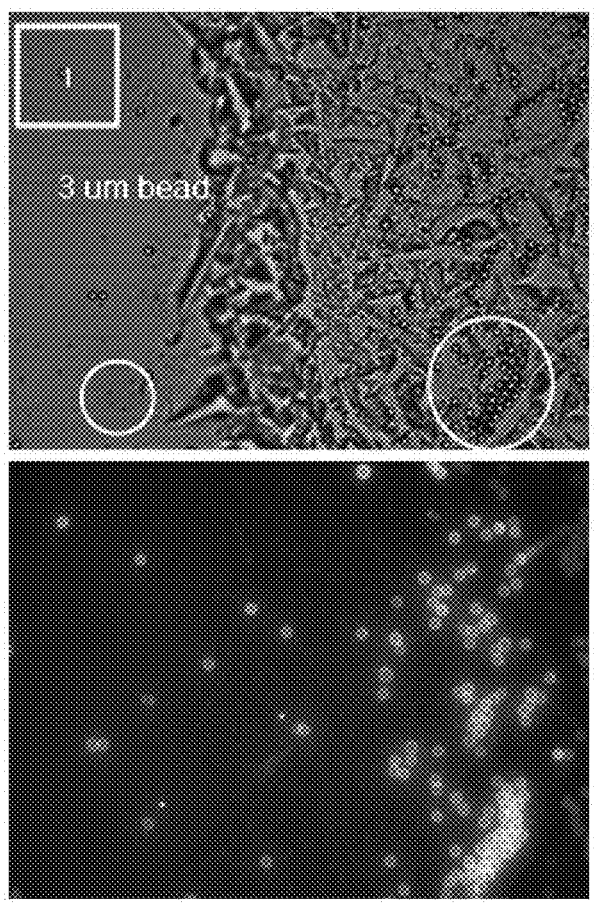
Figure 9:
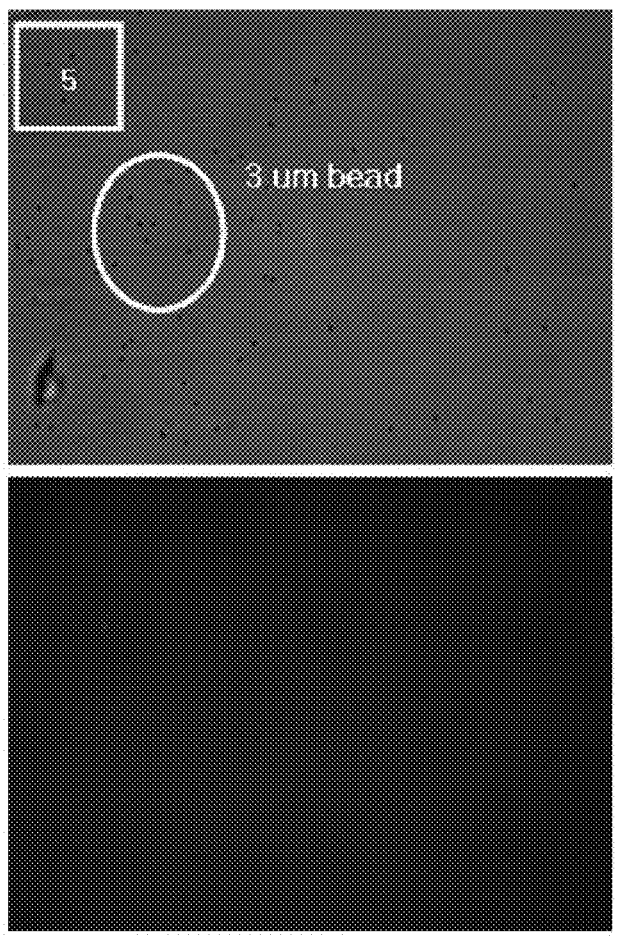
Figure 10:
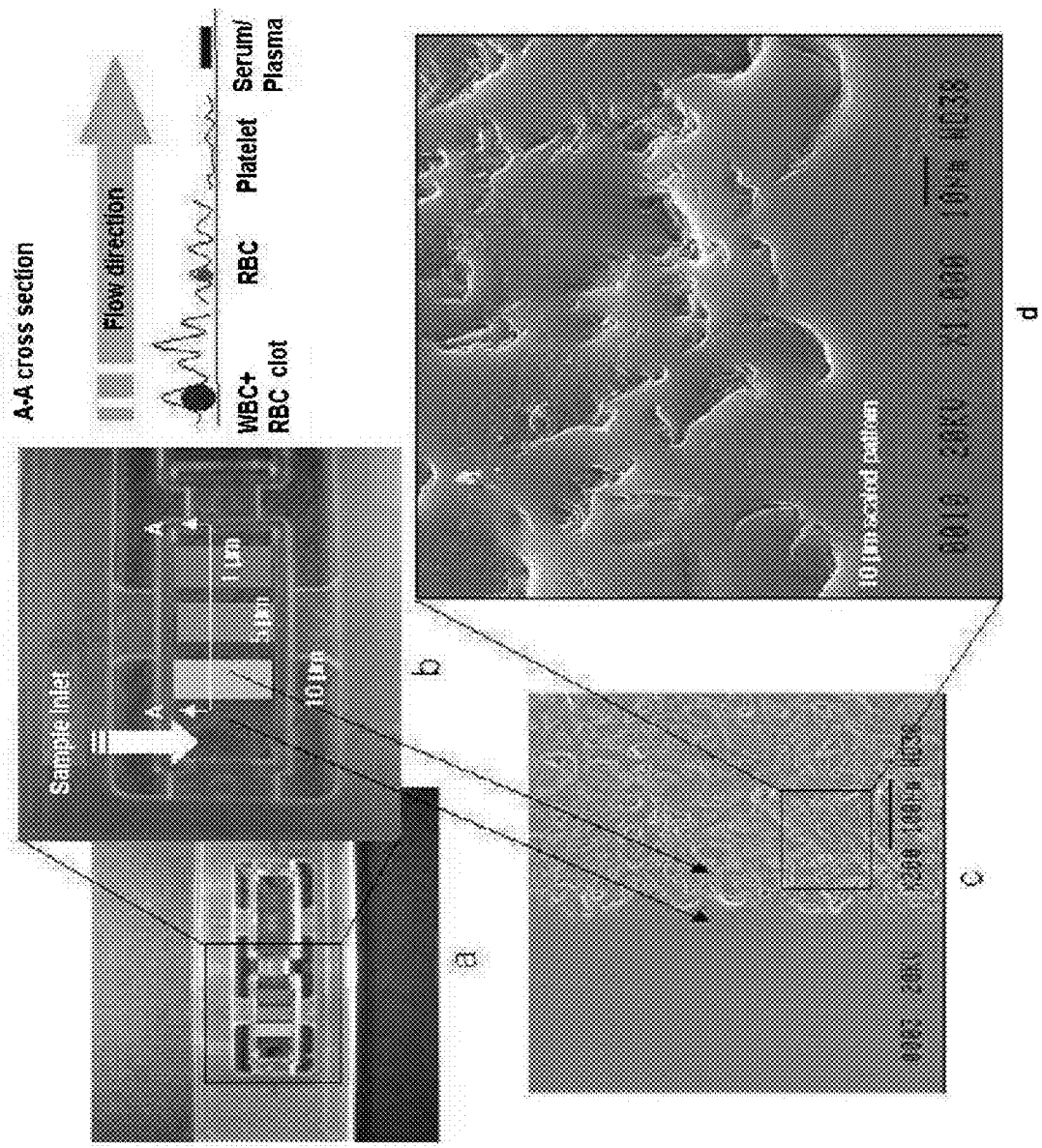
FIG. 10 illustrates an apparatus for separating microparticles by using a microchip filter channel according to the present invention.
Figure 11:
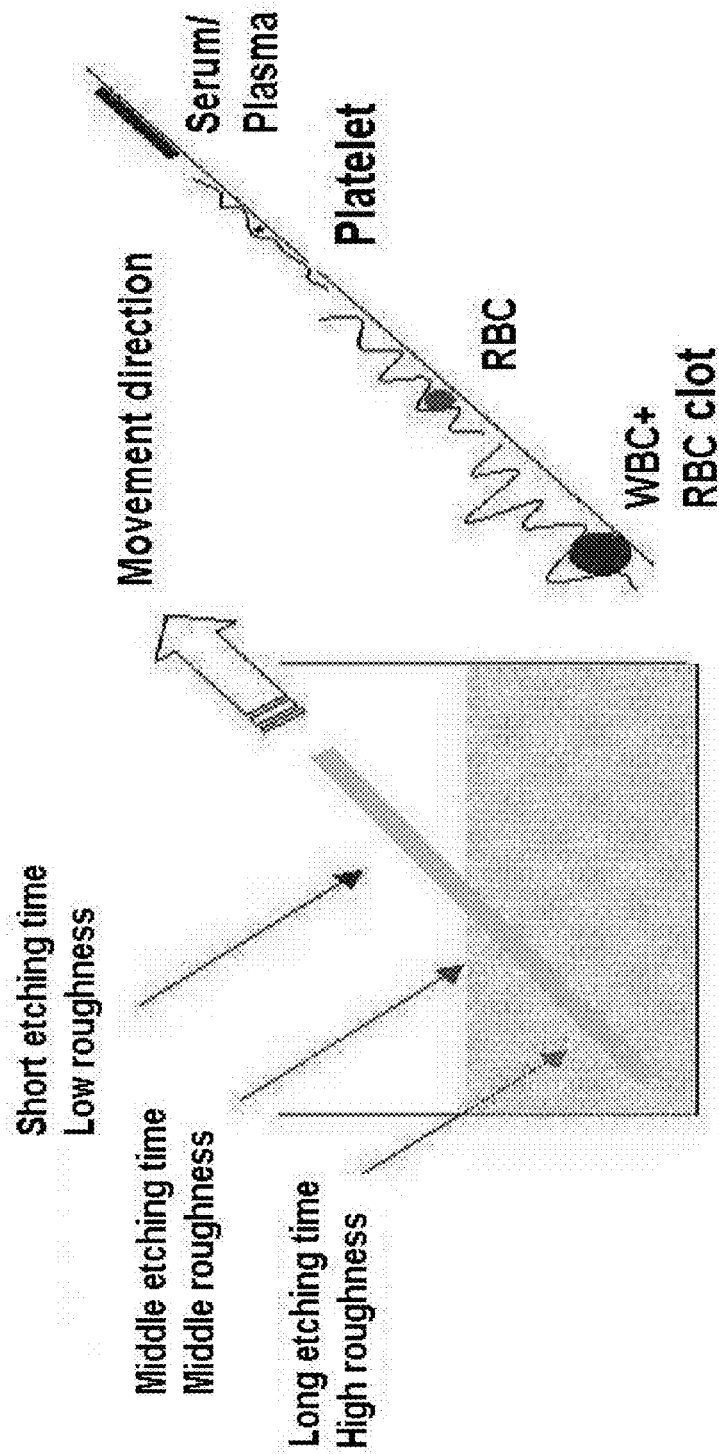
FIG. 11 illustrates a process for manufacturing a microchip filter channel according to the present invention.

Separation of Microparticles from a Mixed Sample of Two Sizes by Using a Channel Filter Having a Topology with a Reference Height of 10 µm A channel filter including a topology with a reference height of 10 µm on the surface of a substrate was made in the same manner as the first example. Mixed liquid of 10 µl was prepared by mixing 5 µl of 10 µm polystyrene beads (the size similar to white blood cells) and 5 µl of 3 µm polystyrene beads (from Polyscience, the size similar to red blood cells) with 0.02% (w/v %). Herein, 10 µm of polystyrene beads are commercially available (Invitron, U.S.), and include an orange fluorescence substance (540/560). On the other hand, 3 µm of polystyrene beads do not include the fluorescence substance. Through the same process as the first example, a microfluidics chip was manufactured. Next, a sample of 5 µl was loaded into a channel filter inlet by a pipette, and was moved to a sample outlet by a capillary action. After the movement, the sample was observed by using an optical microscope (Olympus, x70) and a fluorescence microscope. FIGS. 7 to 9 show the observed result. As shown in FIGS. 7 and 8, before coming to a channel filter, the sample liquid included both of the 3 µm beads and the 10 µm beads. It was found that while the sample was passing through the channel filter, 10 µm beads were filtered by a pattern, and 3 µm beads passed through the filter having a topology pattern. FIG. 7 (2) shows that 10 µm beads were filtered without passing through the filter, and FIGS. 7 to 9 show that only 3 µm beads exist.

The present invention has been described with reference to a preferred embodiment thereof, but it will be understood that changes, obvious to those skilled in the art, may be made within the scope and spirit of the appended claims.

INDUSTRIAL APPLICABILITY

As described above, by using a channel filter according to the present invention, it is possible to easily separate microparticles from a sample including various sized microparticles. In a channel filter according to the present invention, since a height and a width of a surface topology are randomly formed, sample particles trapped by a filter are trapped over the entire filter, thereby preventing pressure drop and sample damage. Also, due to easy and simple manufacturing process, the channel filter according to the present invention can be manufactured with a low cost.

What is claimed is:

1. A channel filter for separating various sized microparticles, wherein the channel filter has a surface topology so that the microparticles are trapped according to their sizes and the microparticles that are moved by a capillary action are sequentially separated according to their sizes,
    wherein the surface topology has a curvilinear shape,
    wherein the surface topology comprises a plurality of individual topologies having various heights corresponding to the sizes of the microparticles in a length direction, from an inlet of the channel through which the microparticles are loaded, to an outlet of the channel through which the microparticles are discharged,
    wherein the surface topology also has various intervals between adjacent individual topologies corresponding to the sizes of the microparticles in a width direction perpendicular to the inlet and the outlet of the channel, and
    wherein individual topologies have a curvilinear shape.

2. The channel filter as claimed in claim 1, wherein the surface topology is continuously or discontinuously formed.

3. The channel filter of claim 1, wherein the channel filter has a surface topology having a continuous or discontinuous inclined reference height corresponding to an average of diameters of the microparticles.

4. The channel filter as claimed in claim 3, wherein the reference height is inclined upward or downward in a movement direction of the microparticles, from an inlet through which the microparticles are loaded, to an outlet through which the microparticles are discharged.

5. A microchip for separating microparticles, the microchip comprising a channel filter as claimed in one of claims 1 to 4.

6. A method for manufacturing a channel filter as claimed in one of claims 1 to 4, the method comprising the step of chemically or physically etching a surface of a channel.

7. A method for manufacturing a channel filter as claimed in one of claims 1 to 4, the method comprising the steps of: manufacturing a mold in such a manner that a surface topology is formed with a certain reference height; and manufacturing the channel filter by injection molding through the mold.

8. The channel filter of claim 1, wherein the channel filter has a surface topology having a continuous/discontinuous downward/upward reference height corresponding to an average of diameters of the microparticles.

* * * * *